US00PP12915P2

(12) United States Plant Patent
Moser

(10) Patent No.: US PP12,915 P2
(45) Date of Patent: Sep. 3, 2002

(54) CHRYSANTHEMUM PLANT NAMED 'DINKA'

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 09/563,808

(22) Filed: May 1, 2000

(51) Int. Cl.[7] ..... A01H 5/00

(52) U.S. Cl. ..... Plt./297

(58) Field of Search ..... Plt./297

*Primary Examiner*—Bruce R. Campell
*Assistant Examiner*—Annette H. Para
(74) *Attorney, Agent, or Firm*—Christie, Parker & Hale, LLP

(57) ABSTRACT

A new plant variety of chrysanthemum producing pink daisy-type flowers with pink ray florets and yellow disc florets.

1 Drawing Sheet

BACKGROUND OF THE INVENTION

The present invention is dircted to a new and distinct variety of *Chrysanthemum morifolium*. The varietal denomination of the new chrysanthemum is 'Dinka'.

The new variety is a cross of two undistributed, unpatented and unnamed seedlings. The new variety has been asexually reproduced by vegetative cuttings in Ventura County, Calif. and the distinguishing characteristics are retained through successive generations of a sexual reproduction.

SUMMARY OF THE INVENTION

'Dinka' is a chrysanthemum plant variety with daisy-type flowers having pink ray florets and yellow disc florets.

COMPARISON WITH OTHER VARIETY

The following is a comparison to the commercial variety 'Temptress' (U.S. Plant Pat. No. 11,866):

| | 'Temptress' | 'DINKA' |
|---|---|---|
| Inflorescence Diameter | 4.5 cm | 3 cm |
| Ray Floret coloration when mature | Near 53D | Near 50A |
| Quantity of Ray florets | About 110 | Between 40 to 50 |
| Approximate quantity of inflorescence per stem | About 10 | About 18 |

BRIEF DESCRIPTION OF ILLISTRATIONS

The accompanying photograph shows a typical specimens of the plant and flowers of the new variety with colors being as nearly true as possible with illustrations of this type.

DESCRIPTION OF THE PLANT

The following description of the new variety is of specimens grown in a greenhouse in Ventura County, Calif. The plant described is approximately 70 days old from a rooted cutting. 'Dinka' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about 10 days after planting. No treatment with growth retardant was used with plants described. Useful growing conditions include average night temperatures of about 170° to 20° C., and average day temperatures of about 20° to 30° F. No susceptibility or resistance to disease was observed. Neither resistance nor susceptibility has been observed concerning insects. Tolerance to cold or drought has not been observed.

Rooting characteristics:
- *Time to initiate roots.*—About 7 to 14 days at about 21° C.
- *Rooting habit.*—Fine, fibrous.

Plant:
- *Plant type.*—Herbaceous perennial.
- *Growth habit.*—Mounding.
- *Height.*—About 24 cm.
- *Growth rate.*—Moderate.
- *Branching characteristics.*—Free branching.

Foliage:
- *Arrangement.*—Alternate.
- *Compound or simple.*—Simple, general outline ovate, shape palmately lobed.
- *Quantity of leaves.*—Many.
- *Leaf size.*—Length: About 4 cm. Width: About 2 cm.
- *Leaf shape.*—Ovate.
- *Leaf tip.*—Acuminate.
- *Leaf base.*—Attenuate.
- *Leaf attachment.*—Stalked.
- *Petiole length.*—About 1.2 cm.
- *Margin type.*—Serrate.
- *Texture.*—Lightly pubescent.
- *Color.*—Young foliage upper side: Near 137C. Young foliage under side: Near 137D. Mature foliage upper side: Near 137A. Mature foliage under side: Near 137B.
- *Venation.*—Color: Venation upper side: Near 137C. Venation under side: Near 137D.

Bloom:
- *Inflorescence.*—Flowering habit: Induced by darkness period greater than 13.5 hours; Approximately 50 days of day length required to induce and develop blooms. Inflorescence form: Daisy. Natural flowering season: Around the last 2 weeks in September. Quantity of inflorescence per stem: About 18. Inflorescence diameter: About 3 cm. Inflorescence depth: About 1.5 cm. Disc diameter: About 1.5 cm. Inflorescence longevity on plant: About 20 to 14 days. Persistence: Persistent.

*Ray florets.*—Appearance: Matte. Texture: Smooth. Number: About 40 to 50. Shape: Oblanceolate. Margin: Entire. Tip: Obtuse. Length: About 1.5 cm. Width: About 1 cm. Color: Upper side: First opening: Near 50A. Mature: Near 50A. Fading: Near 44D. Under side: First Opening: Near 46A. Mature: Near 44C. Fading: Near 44C.

*Disc florets.*—Appearance: Shiny. Texture: Smooth. Number: About 100. Shape: Cylindric. Tip: Obtuse. Length: About 1 cm. Width: About 0.1 cm. Color: First opening: Near 46A. Mature: Near 16A. Fading: Near 22B.

*Pedencle.*—Length: Terminal, shortest: About 4 cm. Lateral, longest: About 6 cm. Color: Near 137C. Strength: Moderate. Habit: Erect.

*Inflorescence bud.*—Length: About 0.8 cm. Diameter: About 1 cm. Form or shape: Globular. Color: Near 13B.

*Involucral bracts.*—Length about 0.6 cm; width about 0.3 cm. Appearance: Matte. Texture: Lightly pubescent. Number: About 30 to 40. Shape: Ovate. Margin: Entire. Tip: Acute. Color: Upper side: Near 137B. Under side: Near 137B.

Reproductive organs:

*Ray florets.*—Pistillate: Pistil number: 1 per flower. Stigma shape: 2 branched. Stigma color: Near 7D. Style length: About 0.6 cm. Style color: Near 6D.

*Disc florets.*—Pistillate: Pistil number: 1 per flower. Stigma shape: Cylindric. Style length: About 0.5 cm.

*Staminate.*—Stamen number: About 5. Anther shape: Tubular. Anther color: Near 14C. Pollen color: Near 16A.

*Seeds.*—Seed production has not been observed.

What is claimed is:

1. A new and distinct chrysanthemum plant of the variety substantially as herein shown and described.

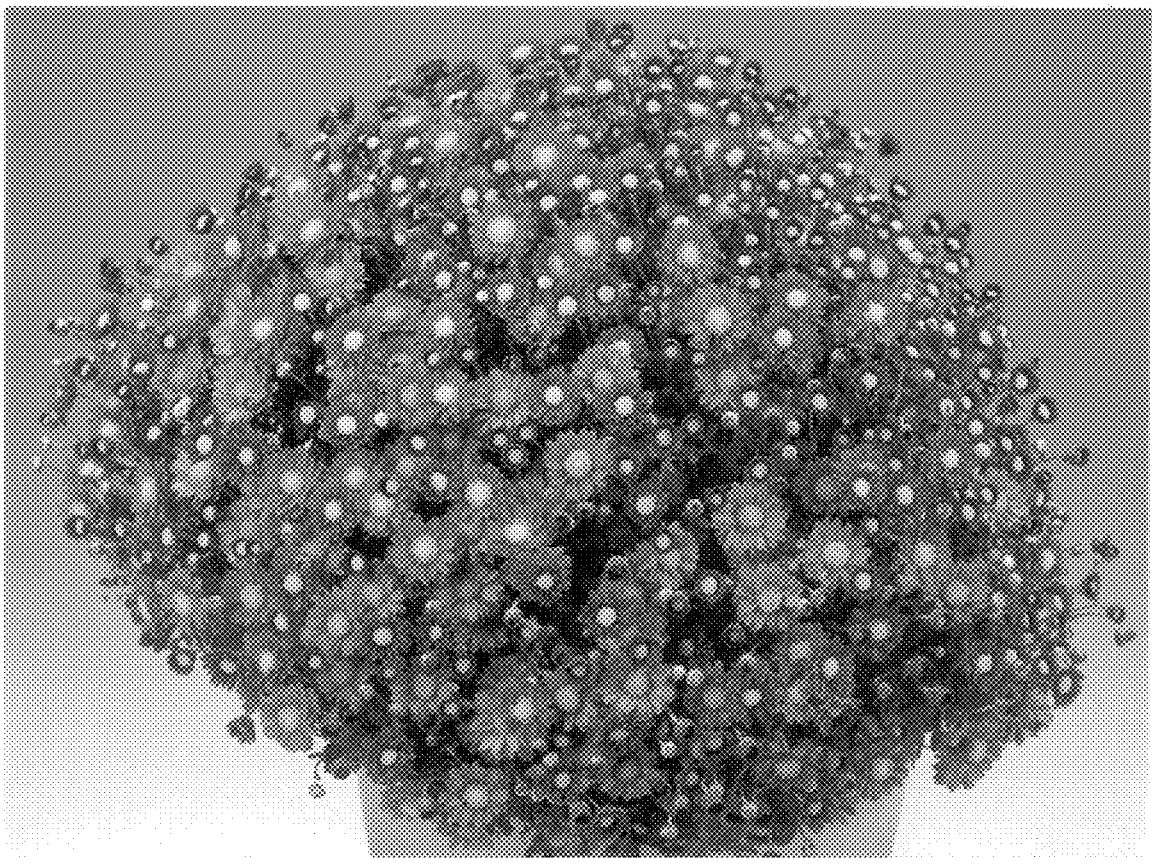

* * * * *